US012763179B2

(12) United States Patent
Abramoff

(10) Patent No.: US 12,763,179 B2
(45) **Date of Patent: *Oct. 13, 2026**

(54) DIRECT MEDICAL TREATMENT PREDICTIONS USING ARTIFICIAL INTELLIGENCE

(71) Applicant: Digital Diagnostics Inc., Coralville, IA (US)

(72) Inventor: Michael D. Abramoff, University Heights, IA (US)

(73) Assignee: Digital Diagnostics Inc., Coralville, IA (US)

(*) Notice: Subject to any disclaimer, the term of this patent is extended or adjusted under 35 U.S.C. 154(b) by 5 days.

This patent is subject to a terminal disclaimer.

(21) Appl. No.: 18/757,298

(22) Filed: Jun. 27, 2024

(65) Prior Publication Data

US 2024/0347159 A1 Oct. 17, 2024

Related U.S. Application Data

(63) Continuation of application No. 17/541,936, filed on Dec. 3, 2021, now Pat. No. 12,051,490.

(51) Int. Cl.
*G16H 20/00* (2018.01)
*G06F 18/214* (2023.01)
(Continued)

(52) U.S. Cl.
CPC ........... *G16H 20/00* (2018.01); *G06F 18/214* (2023.01); *G06T 7/0012* (2013.01); *G16H 50/20* (2018.01)

(58) Field of Classification Search
CPC ...... G16H 20/00; G16H 50/20; G06F 18/214; G06T 7/0012
See application file for complete search history.

(56) References Cited

U.S. PATENT DOCUMENTS 10,115,194 B2 10/2018 Niemeijer et al.
12,051,490 B2 * 7/2024 Abramoff ............ G06T 7/0012
(Continued)

FOREIGN PATENT DOCUMENTS

CN 111052247 A 4/2020
CN 113362944 A 9/2021
(Continued)

OTHER PUBLICATIONS

Abramoff, M. D. et al. "Foundational Considerations for Artificial Intelligence Utilizing Ophthalmic Images." Ophthalmology, Journal Pre-proof, vol. 129, No. 2, Aug. 2021, pp. 1-33.

Abramoff, M. D. et al. "Lessons Learned About Autonomous AI: Finding a Safe, Efficacious, and Ethical Path Through the Development Process." American Journal of Ophthalmology, vol. 214, Jun. 2020, pp. 134-142.

(Continued)

*Primary Examiner* — Khai M Nguyen
(74) *Attorney, Agent, or Firm* — Fenwick & West LLP

(57) ABSTRACT

A device is disclosed herein that receives image data corresponding to an anatomy of a patient. The device applies the image data to one or more feature models trained using training data that pairs anatomical images to an anatomical feature label, and receives, as output from the one or more feature models, scores for each of a plurality of anatomical features corresponding to the image data. The device applies the scores as input to a treatment model, the treatment model trained to output a prediction of a measure of efficacy of a particular treatment based on features of the patient's anatomy. The device receives, as output from the treatment model, data representative of the predicted measure of efficacy of the particular treatment.

20 Claims, 7 Drawing Sheets

(51) Int. Cl.
*G06T 7/00* (2017.01)
*G16H 50/20* (2018.01)

(56) References Cited

U.S. PATENT DOCUMENTS

| | | | | |
|---|---|---|---|---|
| 12,396,695 | B2 * | 8/2025 | Min | A61B 6/504 |
| 2014/0279746 | A1 | 9/2014 | De Bruin et al. | |
| 2015/0238270 | A1 | 8/2015 | Raffy et al. | |
| 2018/0032681 | A1 * | 2/2018 | Aladahalli | G16H 10/60 |
| 2018/0240552 | A1 | 8/2018 | Tuyl et al. | |
| 2019/0180153 | A1 * | 6/2019 | Buckler | G06F 18/29 |
| 2019/0392943 | A1 | 12/2019 | Sorenson et al. | |
| 2021/0248741 | A1 | 8/2021 | Kannengiesser et al. | |
| 2023/0148955 | A1 | 5/2023 | Kwon | |
| 2023/0178200 | A1 * | 6/2023 | Abramoff | G16H 20/00 705/2 |
| 2025/0166185 | A1 * | 5/2025 | Buckler | G06T 7/0012 |

FOREIGN PATENT DOCUMENTS

| | | | |
|---|---|---|---|
| EP | 1916624 | B1 | 11/2016 |
| WO | WO-2023/064957 | A1 | 4/2023 |

OTHER PUBLICATIONS

PCT International Search Report and Written Opinion, PCT Application No. PCT/US2022/51624, May 25, 2023, 11 pages.

PCT Invitation to Pay Additional Fees, PCT Application No. PCT/US2022/51624, Mar. 1, 2023, 2 pages.

United States Office Action, U.S. Appl. No. 17/541,936, filed Jan. 25, 2024, 12 pages.

Korean Intellectual Property Office, Office Action, Korean Patent Application No. 10-2024-7020549, Mar. 16, 2026, 14 pages.

Canadian Intellectual Property Office, Office Action, Canadian Patent Application No. 3,240,849, May 28, 2026, seven pages.

* cited by examiner

DIRECT MEDICAL TREATMENT PREDICTIONS USING ARTIFICIAL INTELLIGENCE

CROSS REFERENCE TO RELATED APPLICATIONS

This application is a continuation of co-pending U.S. patent application Ser. No. 17/541,936, filed Dec. 3, 2021, which is incorporated by reference herein in its entirety.

BACKGROUND

This invention relates generally to using artificial intelligence (AI) to directly determine a patient specific treatment or management of a disease that will benefit that patient, rather than manual selection based on a diagnosis. Currently, autonomous AI systems use machine learning or other optimization techniques to determine the diagnosis of a patient, and clinicians then use this AI diagnosis, in addition to other relevant patient and population information, to subjectively determine patient specific management or prescribe a patient specific treatment (also referred to herein as an "intervention"). Thus, Autonomous AI diagnosis, while capable of determining a diagnosis without human oversight, still relies on a clinician to interpret the diagnosis in terms of the patient's entire case and then decide the intervention. However, this intermediate, subjective decision step is subject to high inter- and intra clinician variability, temporal and other drift. Moreover, the interaction between artificial intelligence and the clinician is variable with often unanticipated risks, and has been known to worsen rather than improve outcome. Moreover, obtaining the highest quality reference standard ('ground truth') to train autonomous AI models for producing a diagnosis can be ethically problematic, and expensive. Where the reference standard is dependent on clinician expertise, such as subjective reading of images, the reference standard can be noisy. Instead, when clinical outcome, (which combines the effects of both the accuracy of the diagnostic process as well as the precision of the treatment or management selection process) rather than the interim diagnosis can be used as reference standard for training the AI, this subjective, noisy step is eliminated, with the potential to have higher performance.

SUMMARY

Systems and methods are disclosed herein that use machine learning to output indicia of whether a patient will benefit from a specific intervention (e.g., in terms of clinical outcome), without first requiring prediction of a diagnosis for the patient. Advantageously, the disclosed systems and methods remove a need for a subjective and noisy clinician interpretation of a diagnostic output, as the disclosed machine learning models directly output whether a specific patient will benefit from a specific intervention, which may be a binary recommendation or prescription, or a likelihood or other probabilistic output. Yet further, fewer resources are needed for validation of an intervention, and patient risk of harm is lower, as validating a diagnosis from artificial intelligence typically involves expensive experts, radiation, or other potentially harmful processes for both cases and normal, and efforts in combining their decisions, while determining how much a patient benefitted is a low cost survey. Moreover, obtaining truth data as to whether a patient benefitted can be much more accurate than doing so for diagnoses, as clinical outcome is typically far easier to observe than accurately diagnosing a condition.

In an embodiment, a device receives sensor data from an electronic device that monitors a patient. The device accesses a machine learning model, the machine learning model trained using training data that pairs information about patients to labels that describe whether a particular treatment yielded a positive result. The device applies the sensor data to the machine learning model, and receives, as output from the machine learning model, data representative of a likelihood that a patient would benefit from one or more treatments.

In an embodiment, a device receives image data corresponding to an anatomy of a patient. The device applies the image data to a feature extraction model trained using training data that pairs anatomical images to an anatomical feature label, and receives, as output from the feature extraction model, scores for each of a plurality of anatomical features corresponding to the image data. The device applies the scores as input to a treatment model, the treatment model trained to output a prediction of a likelihood of efficacy of a particular treatment based on features of the patient's anatomy as described in the data structure. The devices then receives from the treatment model data representative of the predicted likelihood of efficacy of the particular treatment. Advantageously, the treatment model does not have access to the image data, thus ensuring that the treatment model is not using information from the images that might bias a determination (e.g., skin color, gender information, and so on).

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

(a) Overview

Figure 1:
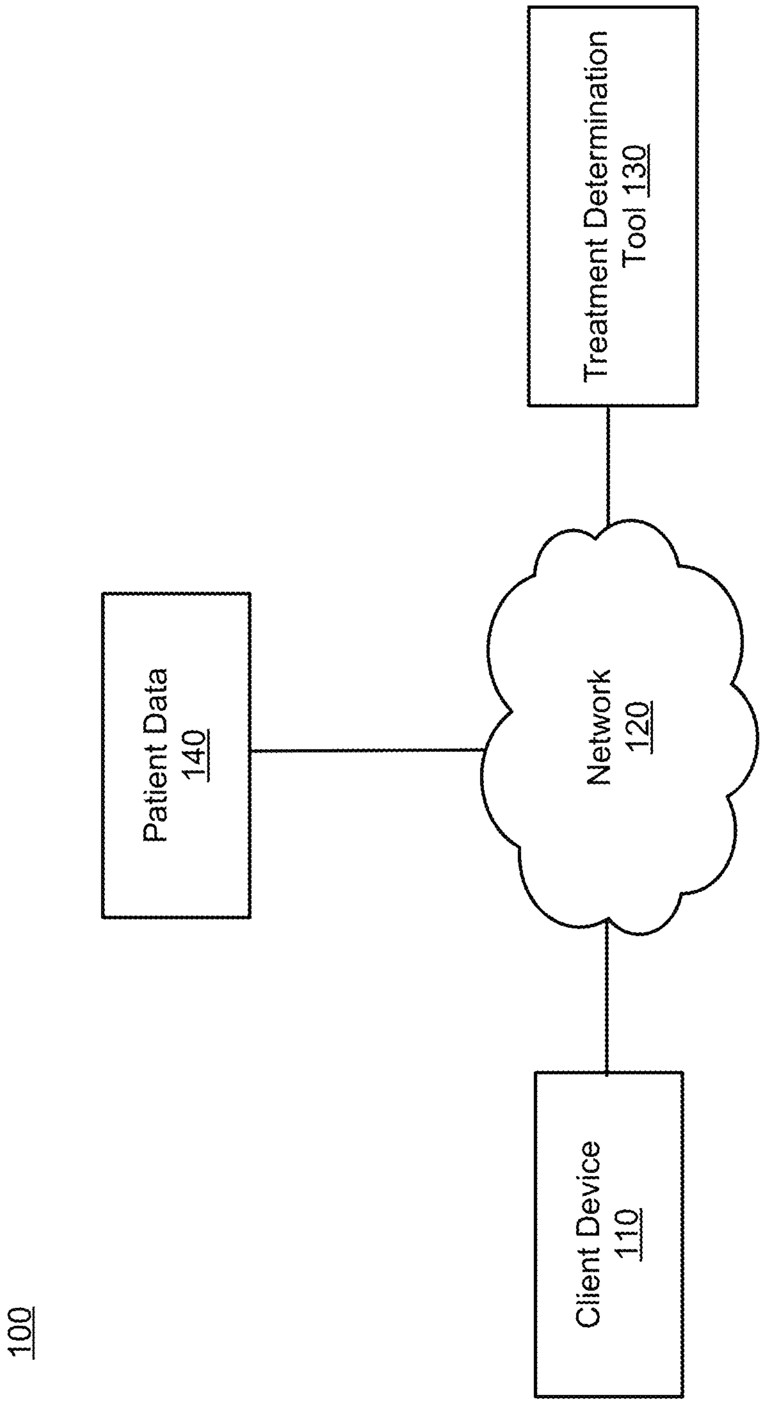
FIG. 1 illustrates one embodiment of a system environment for implementing a treatment determination tool.

FIG. 1 illustrates one embodiment of a system environment for implementing a treatment determination tool. As depicted in FIG. 1, environment 100 includes client device 110, network 120, treatment determination tool 130, and patient data 140. The elements of environment 100 are merely exemplary; fewer or more elements may be incorporated into environment 100 to achieve the functionality disclosed herein.

Client device 100 is a device in which inputs of patient data may be provided, and where one or more recommended treatments for a patient may be output, the treatments determined by treatment determination tool 130. The term patient data, as used herein, may refer to any data describing a patient, including images of a patient's anatomy, biometric sensor data, doctor's notes, and so on. Client device 110 may run an application installed thereon, or may have a browser installed thereon through which an application is accessed, the application performing some or all functionality of treatment determination tool 130 and/or communicating information to and from treatment determination tool 130. The application may include a user interface through which a user can input data into client device 110. The user interface may be graphical, where the user can input patient data manually (e.g., through a keyboard or touch screen). The user interface may additionally or alternatively be a biometric sensor, where patient data is automatically sensed and transmitted by the application to treatment determination tool 130. The user interface may be used to access existing patient data stored in patient data 140, which may then be communicated to treatment determination tool 130 for processing.

Client device 110 may be any device capable of transmitting data communications over network 120. In an embodiment, client device 110 is a consumer electronics device, such as a laptop, smartphone, personal computer, tablet, personal computer, and so on. In an embodiment, client device 110 may be any device that is, or incorporates, a sensor that senses patient data (e.g., motion data, blood saturation data, breathing data, or any other biometric data).

Network 120 may be any data network capable of transmitting data communications between client device 110 and treatment determination tool 130. Network 120 may be, for example, the Internet, a local area network, a wide area network, or any other network.

Treatment determination tool 130 receives patient data from client device 110 and outputs a treatment from which the patient is likely to improve. Further details of the operation of treatment determination tool 130 are discussed below with reference to FIG. 2. Operations of treatment determination tool 130 may be instantiated in whole or in part on client device 111 (e.g., through an application installed on client device 110 or accessed by client device 110 through a browser).

Patient data 140 is a database that houses records of data of one or more patients. Patient data 140 may be hospital records, personal records of a patient, doctors notes, and so on. Patient data 140 may be co-located at client device 110 and/or at treatment determination tool 130.

Figure 2:
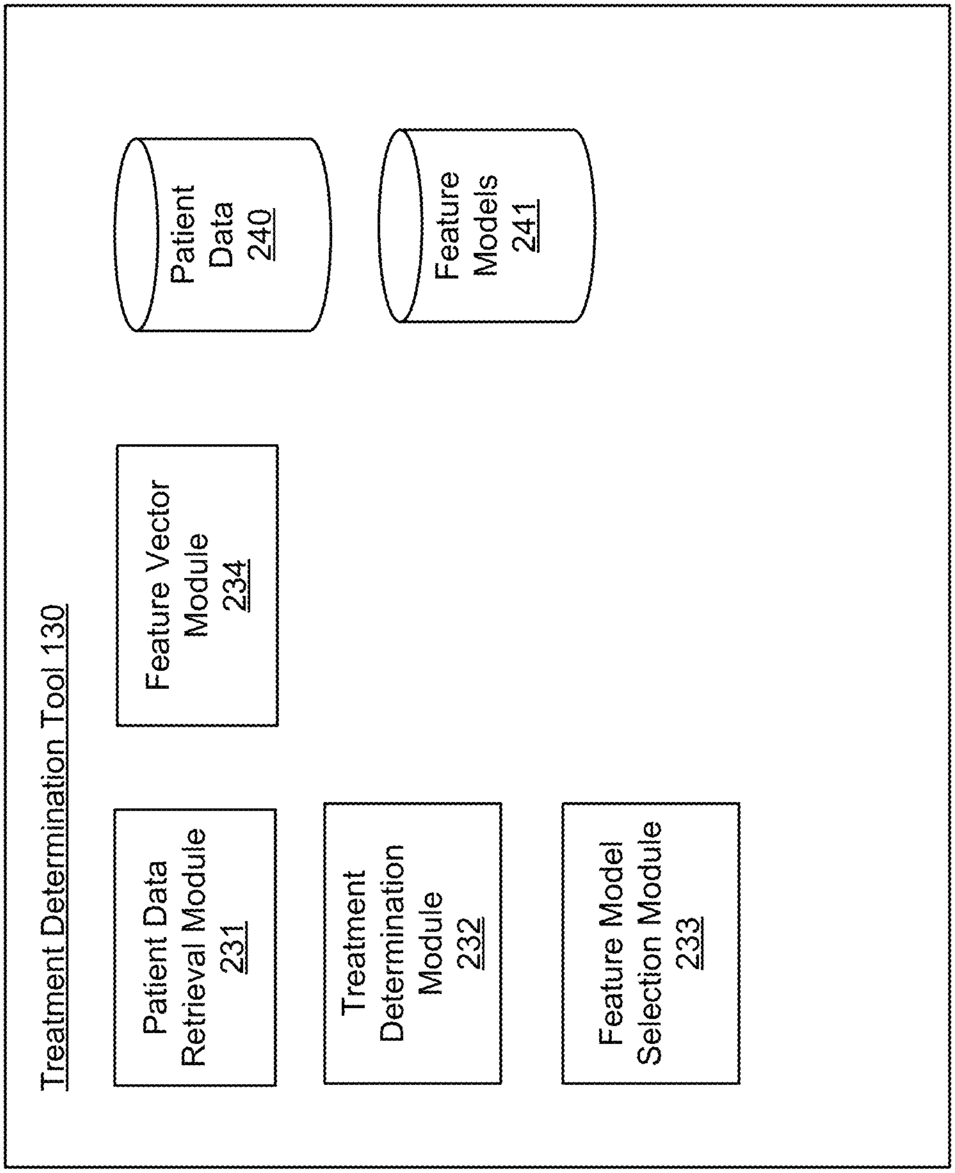
FIG. 2 illustrates one embodiment of exemplary modules and databases used by the treatment determination tool in using artificial intelligence to directly output a treatment.

FIG. 2 illustrates one embodiment of exemplary modules and databases used by the treatment determination tool in using artificial intelligence to directly output a treatment. As depicted in FIG. 2, treatment determination tool 130 includes patient data retrieval module 231, treatment determination module 232, feature model selection module 233, feature vector module 234, patient data 240, and feature models 241. The modules and databases depicted in FIG. 2 are merely exemplary; treatment determination tool 130 may include more or fewer modules and/or databases and still achieve the functionality described herein. Moreover, the modules and/or databases of treatment determination tool 130 may be instantiated in whole, or in part, on client device 110 and/or one or more servers.

Patient data retrieval module 231 receives patient data (e.g., from client device 110 and/or patient data 140). In two exemplary embodiments, the patient data may be image data corresponding to an anatomy of a patient, or may be sensor data from an electronic device that monitors a patient. While these exemplary embodiments will be the subject of detailed treatment in this disclosure, any other form of patient data may be received by patient data retrieval module 231.

Treatment determination module 232 accesses one or more machine learning models, applies the received patient data to the one or more machine learning models, and receives as output from the one or more machine learning models data representative of a predicted measure of efficacy of one or more treatments. Focusing on the embodiment where the received patient data includes image data, FIG. 3 illustrates one embodiment of a multi-stage model that is used to output treatments.

Figure 3:
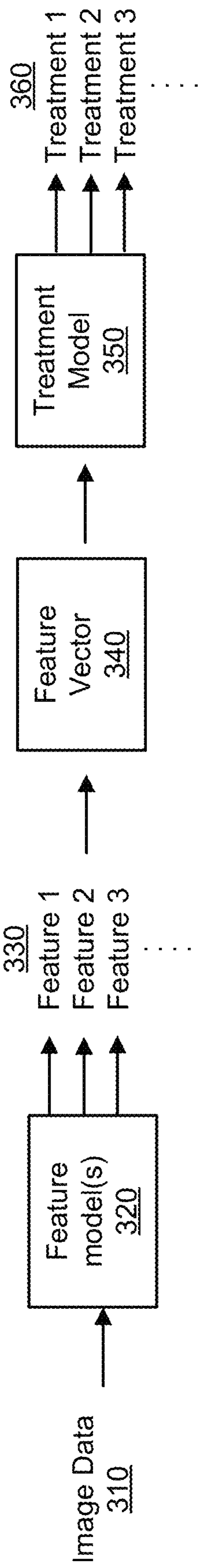
FIG. 3 illustrates one embodiment of a multi-stage model that is used to output treatments.

As depicted in FIG. 3, image data 310 is received (e.g., from client device 110 or patient data 240). The term image data, as used herein, may refer to images captured using an image sensor. The images may be any type of image, for example including grayscale images, red-green-blue images, infrared images, x-ray images, optical coherence tomography images, sonogram images, or any other type of image. The image data corresponds to an anatomy of a patient. That is, the images include, at least in part, a depiction of a human being. The feature may be external (e.g., skin, eyes, etc.) or internal (e.g., an image of an organ, such as a retina or a liver).

Treatment determination module 232 applies the image data to one or more feature models 320 (e.g., accessed from feature models 241). The image data may include data from one or more images. The term feature model (or "feature extraction model"), as used herein, may refer to a model trained to identify or extract one or more features in an image. The term "feature model" and "feature extraction model" are used interchangeably herein. Where used in the singular, a "feature model" or "feature extraction model" may refer to a single model or an ensemble of two or more models. The term feature, as used herein, may refer to an object within an image. Objects may include anatomical objects (e.g., a blood vessel, an organ (e.g., optic nerve), and so on. Objects may also include biomarkers, which may be anomalies, such as lesions, fissures, dark spots, and any other abnormalities relative to a normal anatomic part of a human being. The feature model(s) may be trained using labeled training images, where the training images show at least portions of human anatomy, and are labeled with at least a score (e.g., likelihood or probability) of whether the image includes a biomarker (e.g., feature). The labels are also referred to herein as anatomical feature labels. The training images are also referred to herein as anatomical images. In an embodiment, the labels may include an identification of one or more specific biomarkers within the image. The labels may include additional information, such as other objects within the images and one or more body parts that the training image depicts. Further discussion of the structure, training, and use of feature models is disclosed in commonly-owned U.S. Pat. No. 10,115,194, filed Apr. 6, 2016, issued Oct. 30, 2018, the disclosure of which is hereby incorporated by reference herein in its entirety.

In an embodiment, data additional to the image data is input into the feature model(s) 320. The additional data may be any patient data. In such an embodiment, the training data for the feature model(s) 320 may include a pairing of images with other patient data. For example, blood pressure data, oxygen saturation data, and so on, may be included with a training image. Feature model(s) 320 output probabilities that one or more features exist in the image data, or directly output binary decisions that features do or do not exist in the image data based on the probabilities exceeding corresponding thresholds. In embodiments where the feature model(s) 320 are trained to accept additional patient data as input, probabilities may be more accurately assessed, thus enabling a more accurate assessment of whether a feature exists within input image data.

In an embodiment, image data 310 is applied to a single feature model 320 by treatment determination module 232, and the single feature model 320 outputs data representative of one or more corresponding features. As mentioned above, this data may include probabilities that the image data includes one or more features, or may include a binary determination that certain feature(s) are included in the image data.

In an embodiment, image data 310 is applied to a plurality of feature models 320 by treatment determination module 232. Returning momentarily to FIG. 2, feature model selection module 233 may select one or more of feature models 320 to which given images of the image data are to be applied. In an embodiment, feature selection module 223 may determine a body part to which input image data corresponds. Feature models 320 may be any machine learning models such as deep learning models, convolutional neural networks (CNNs), ensemble models, biomarker based systems of a plurality of machine learning models, and so on. The feature models 320 may each correspond to one or more respective body parts. Feature model selection module 223 may, in this case, input image data into the one or more feature models that correspond to a body part to which the image data corresponds. For example, where images are taken of a retina, where one image includes an optic disk, one image includes a fovea, and one image includes both, these images may respectively be applied to a feature model for an optic disk, a feature model for a fovea, and both models. More granular data may be used, such as a particular body part within a body part, or a location of a body part or object within an image. For example, images that are centered around an optic disk may be applied to one feature model, and images that are centered around a fovea may be applied to another feature model, notwithstanding that some of the images may include both an optic disk and a fovea. Feature models 320 may be selected by feature selection module 223 on bases other than a body part depicted in an image, such as on any other characteristics of the patent or disease (e.g., a specific age range, a disease requiring analysis of both the ear and the bladder, and so on). In an embodiment, other patient data applied to feature models 320 may be used by feature model selection module 223 to select a feature model to apply an image (e.g., a scenario where multiple feature models are trained for a given body part, but are tuned using different patient data).

As discussed above, treatment determination module 232 determines features 330 based on output from feature model(s) 320. Feature vector module 234 consolidates features 330 into feature vector 340. The term feature vector, as used herein, may refer to a data structure that includes each of the different features. The feature vector may map the different features to auxiliary information. For example, where the image data includes images corresponding to different locations of a body part, the feature vector may map the features identified from those images to their respective different locations of the body part. As an example, where the images are retinal images, and one image is taken for each quadrant of a retina, the feature vector may include four data points, the data points including respective features identified in an image of each of the four quadrants.

Treatment determination module 232 applies feature vector 340 to treatment model 350. Treatment model 350 is trained to, based on an input feature vector, output a prediction of a measure of efficacy of one or more particular treatments for a patient based on features of the patient's anatomy as described in the data structure. Treatment model 350 may be any machine learning model (e.g., deep learning model, convolutional neural network (CNN), etc.). The training data may include data manually labeled by patients, where patients indicate that they felt better or did not feel better after a treatment, and where this manual label is paired to image feature vectors, optionally with other patient data, to a label corresponding to what the patient has indicated. The labels may alternatively, or additionally, be manually labeled by doctors. In an embodiment, patient data, such as vitals or descriptors of patient health, may be monitored from a time of treatment. The patient data may be compared to data from prior to the time of treatment. The monitoring both before and after the time of treatment may be bounded by a maximum threshold amount of time. Responsive to determining that the patient data shows an improvement, the feature vectors may be labeled with the treatment and an indicator that the patient has improved. Similarly, images may be labeled showing no improvement, or a worsening condition, based on the monitored patient data. In an embodiment, a degree to which a patient improved or worsened may be labeled against images and/or feature vectors. In some embodiments, the labeling of training data might be automatic, where patient data and/or disease data and/or treatment data is labeled with outcome These labels may alternatively be manually applied (e.g., by clinicians monitoring patient response to treatment).

Treatment determination module 232 receives, as output from treatment model 350, a prediction of a measure of efficacy (e.g., a likelihood that a treatment will be efficacious for a patient, according to a predetermined criteria therefor) of one or more particular treatments for a patient based on features of the patient's anatomy as described in the data structure. Like the output of feature model(s) 320, treatment model 350 may output probabilities corresponding to a predicted efficacy of a plurality of candidate treatments, or alternatively, may directly output identifiers of treatments having probabilities that exceed a threshold. Treatment determination module 232 determines, based on the output of treatment model 350, one or more treatments that are likely to be effective for a patient, and outputs the determined one or more treatments to a user (e.g., a doctor, a patient, or another medical clinician).

In some embodiments, rather than using a two-stage model as depicted in FIG. 3, a single stage model may be used to directly predict effective treatments for a patient based on underlying patient data. Exemplary single-stage models are discussed with reference to FIGS. 4 and 5; however, these are merely representative, and any form of machine learning model trained to output a treatment directly based on patient data may be used to determine one or more effective treatments for a patient.

Figure 4:
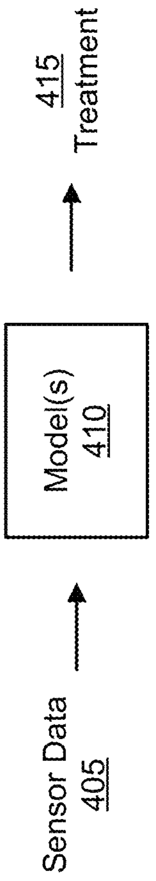
FIG. 4 illustrates one embodiment of a single-stage model that is trained to output treatments based on input sensor data.

FIG. 4 illustrates one embodiment of a single-stage model that is trained to output treatments based on input sensor data. As depicted in FIG. 4, sensor data 405 is received from a patient. Patient data retrieval module 231 may receive the sensor data. The term sensor data, as used herein, may refer to data obtained from a sensor that is monitoring physical attributes of a patient. Exemplary sensors may include sensors include electroencephalogram (EEG) sensors, motion sensors, imaging of the retina or outer ear canal, breathing sensors, image sensors, video sensors, acceleration data, and so on.

Treatment determination module 232 applies sensor data 405 into treatment model 410, which may be any machine-learned model described herein (e.g., a CNN). Treatment model 410 may be trained using historical sensor data (in isolation and/or in combination with other historical sensor data) as labeled by treatment outcome. In an embodiment, the labels may be manually applied. In another embodiment, the patient's condition may be monitored before and after treatment (e.g., as bounded by a threshold period of time on either or both sides), and a label may be determined automatically from indicia of the condition improving, staying the same, or worsening following treatment. Similar to model 350, treatment model 406 outputs data representative of efficacy of treatment 415, and treatment determination module 232 determines a treatment that is likely to be effective in treating the patient therefrom and provides identifications of those determined treatment(s) to a user. In some embodiments, model 410 may be trained to output multiple treatments. In some embodiments, different ones of model(s) 410 are used to determine different treatments.

Figure 5:
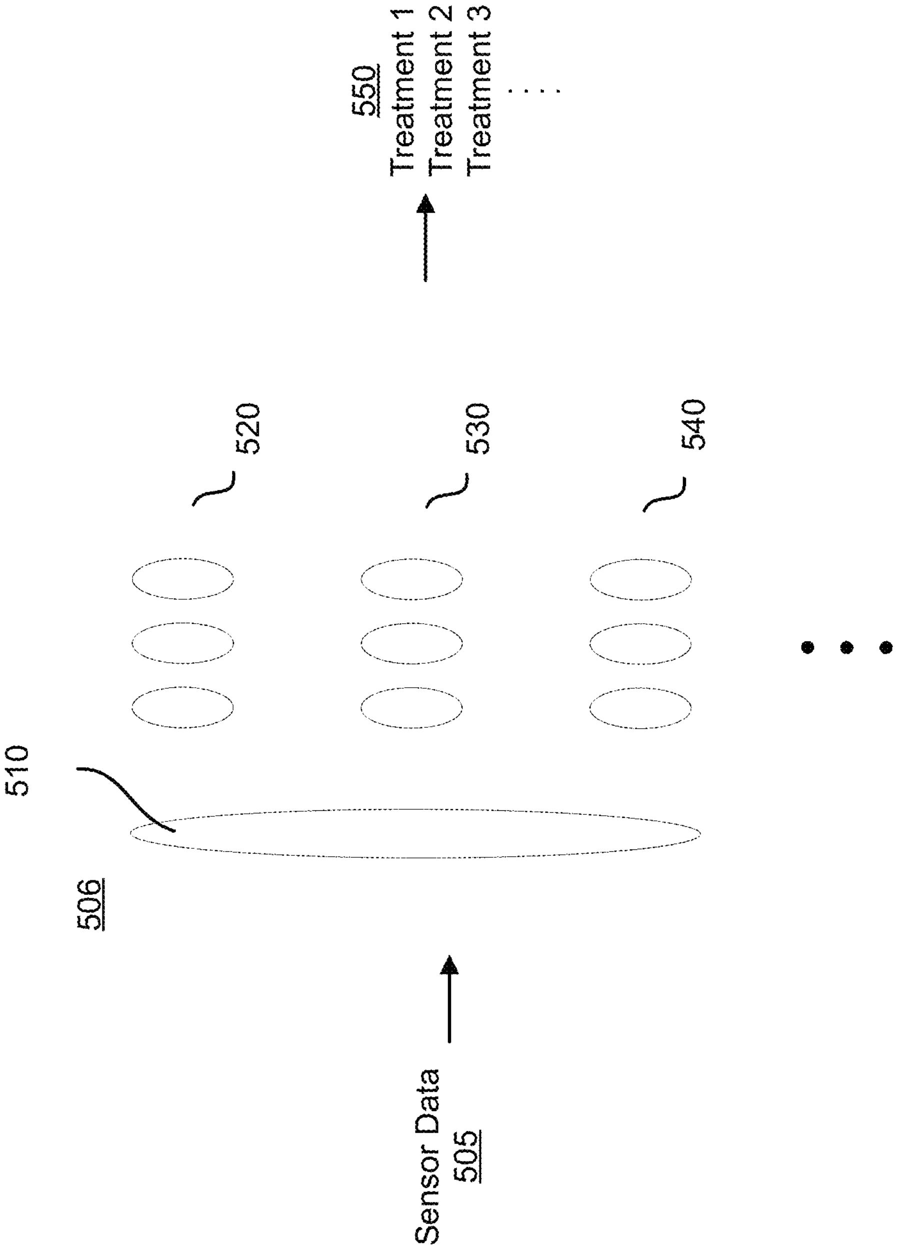
FIG. 5 illustrates one embodiment of a multi-task model, having branches tuned to outputting different treatments, as well a shared layer that is used to fit patient data.

FIG. 5 illustrates one embodiment of a multi-task model, having branches tuned to outputting different treatments, as well a shared layer that is used to fit patient data. In general, treatment determination tool 130 receives sensor data 505 and applies it to treatment model 506, yielding output treatments 550, in the same manner described with respect to like reference numerals in FIG. 4. Treatment model 506, as depicted, is a multi-task model having shared layer 510, and branches 520, 530, and 540. Shared layer 510 is trained using training data for each of branches 520, 530, and 540. Branches 520, 530, and 540 are each trained to output a probability of efficacy of a different one of treatments 550. For example, where a patient is struggling to breathe, branch 520 may output a probability that a CPAP machine would aid the patient, branch 530 may output a probability that taking more oxygen would aid the patient, and branch 540 may output a probability that a biopsy of the lungs would benefit the patient. Like FIG. 4, while three branches are depicted, any number of branches may be used.

The model 506 is trained using training data that indicates input sensor data paired with labels indicating whether a patient associated with that sensor data improved or worsened after receiving the treatment associated with one of the branches of the model 506. Accordingly, the training data includes different sets of training data, each set having the same inputs (e.g., sensor data) but a different label corresponding to efficacy of a different treatment. During training, a training example from one of the sets of training data is selected, and a standard back propagation is performed through the branch (520, 530, or 540) of the model 506 corresponding to the treatment for the selected example and through the shared layers 510 of the model 506. This process is repeated, ultimately selecting training examples from each set and thereby training each of the branches 520, 530, and 540 of the model 506. In an embodiment, back propagation occurs from clinical outcome, through treatment choices, back to diagnostic choices. Back propagation may occur through any layer or branch and may selectively omit layers or branches.

In some embodiments, the different training sets used to train the different branches of the multi-task model may differ substantially in terms of size. This may be a result of some treatments being used frequently among patients, and other treatments being used far less frequently, thus resulting in less training data for a given label of a given training set. The treatment determination tool 130 may sample from the different training sets by a ratio of the available training data across the different training sets. This way, the treatments for which there is relatively less training data benefit from treatments where there is relatively more, since the training data for all of the sets is used for the shared layers 510. This may enable a model to be trained for a treatment that would not otherwise have enough training data to train its own model, as the branch for that treatment is aided by the work done by the shared layers 510.

Technical benefits are thus achieved from using a multi-task model (e.g., neural network) as shown in FIG. 5, as opposed to using separate neural networks for each treatment. In addition to reducing required processing power by distributing redundant processing across multiple neural networks, accuracy is improved for treatments where only a small amount of training examples exist. By training a shared layer (e.g. layer 510) with training data for multiple treatments, the shared layer brings the overall model 506 close for a given treatment corresponding to a given branch, and does so with relatively less training data than is available for the other branches. Further training of that given branch fine-tunes the prediction for that treatment.

Figure 6:
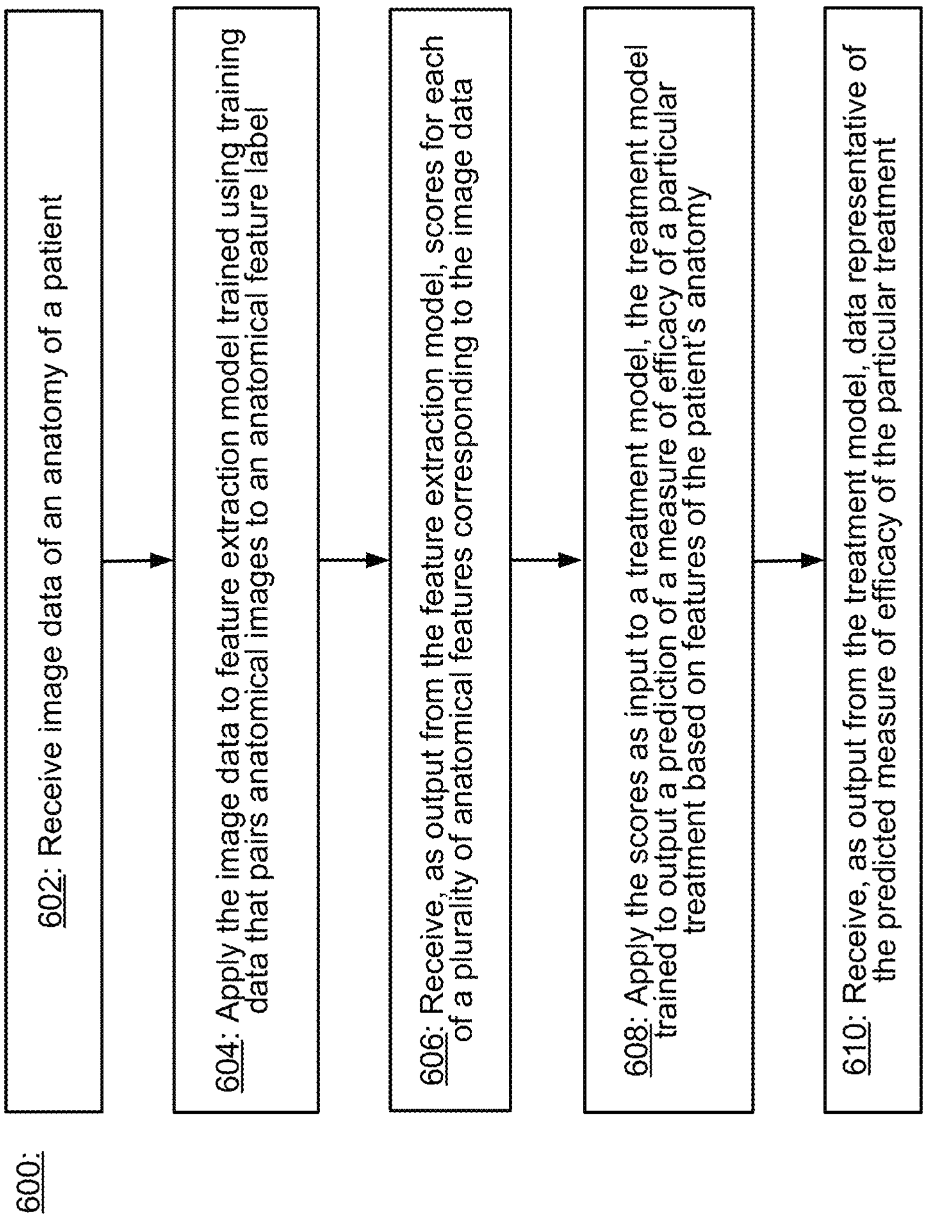
FIG. 6 is a flowchart of an exemplary process for using a multi-stage model that directly outputs treatments, in accordance with an embodiment.

FIG. 6 is a flowchart of an exemplary process for using a multi-stage model that directly outputs treatments, in accordance with an embodiment. Process 600 begins with treatment determination tool 130 receiving 602 image data corresponding to an anatomy of a patient (e.g., using patient data retrieval module 231). Treatment determination tool 130 applies 604 the image data to a feature extraction model trained using training data that pairs anatomical images to an anatomical feature label (e.g., using treatment determination module 232, and applying the image data to one or more of feature models 241). Treatment determination tool 130 receives 606, as output from the feature extraction model, scores (e.g., probability or likelihood) for each of a plurality of anatomical features corresponding to the anatomy, and optionally combines the scores for the plurality of anatomical features into a data structure (e.g., using feature vector module 234). Treatment determination tool 130 applies 608 the scores (e.g., via the data structure if used) as input to a treatment model (e.g., treatment model 350), the treatment model trained to output a prediction of a measure of efficacy of a particular treatment based on features of the patient's anatomy (e.g., as described in the data structure). Treatment determination tool 130 receives 610, as output from the treatment model, data representative of the predicted measure of efficacy of the particular treatment (e.g., representative of treatments 360).

Figure 7:
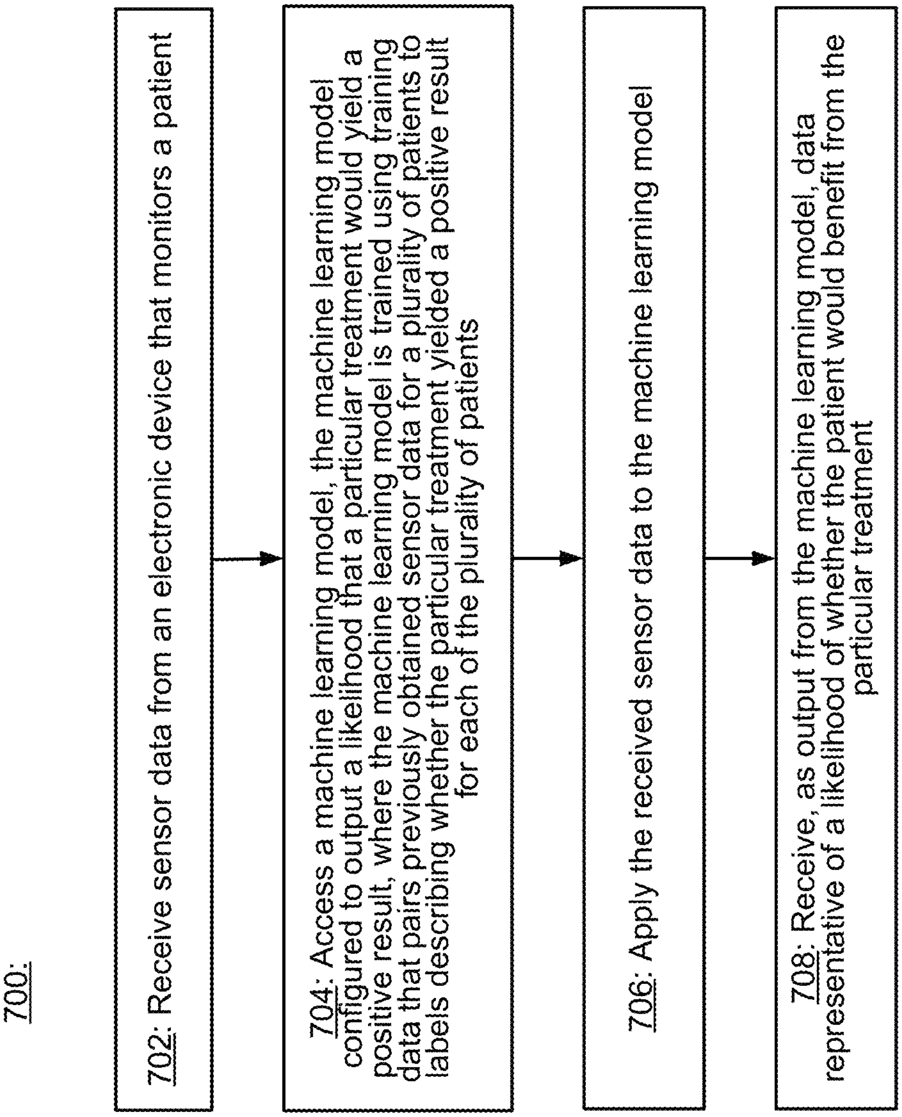
FIG. 7 is a flowchart of an exemplary process for using a single-stage model that directly outputs treatments, in accordance with an embodiment.

FIG. 7 is a flowchart of an exemplary process for using a single-stage model that directly outputs treatments, in accordance with an embodiment. Process 700 begins with treatment determination tool 130 receiving 702 sensor data from an electronic device that monitors a patient (e.g., using patient data retrieval module 231). Treatment determination tool 130 accesses 704 a machine learning model (e.g., model 506), the machine learning model configured to output a likelihood that a particular treatment would yield a positive result, where the machine learning model is trained using training data that pairs previously obtained sensor data for a plurality of patients to labels describing whether the particular treatment yielded a positive result for each of the plurality of patients. Treatment determination tool 130 applies 706 the received sensor data to the machine learning model and receives 708, as output from the machine learning model, data representative of a likelihood of whether the patient would benefit from the particular treatment (e.g., representative of treatments 550).

The above disclosures lead to patient benefit where patients suffer from any number of conditions. For example, where a patient has a sleep apnea condition, the condition may be autonomously diagnosed, where a model is trained using sleep study data such as EEG data, motion data, breathing data, and the like, where the model may output a sleep apnea diagnosis. This enables a clinician to prescribe treatment (e.g., that the patient should use a CPAP machine). Advantageously, the systems and methods disclosed herein remove the need for a diagnosis—a prediction that CPAP will help the patient is directly output without a diagnosis. The benefit from CPAP is determined with fewer computational resources and without a need for a doctor—if the patient's saturation goes up, then CPAP benefitted the patient, and thus ground truth data for using CPAP resulting in a benefit in this example is easily obtained without clinicians having to manually examine input data and decide whether a patient has sleep apnea in the first place. The systems and methods disclosed herein also has an advantage of process integrity, in that it leads to maximizing the population benefit of CPAP machines.

As another example, where a patient has an ear infection, rather than output that a patient has a "otitis media" diagnosis (which requires validation by a physician, followed by a prescription), or a specific prescription of "amoxicillin 200 mg", the system may directly output that "patient benefits from amoxicillin." This may be based on training data showing whether ear infections by patients with similar patient data is labeled based on whether those patients benefitted from amoxicillin at all. Again, obtaining ground truth training data for such a model requires far less cost, as the benefit to patients is self-validating. In some embodiments, for this reason, outputs of models may be dichotomous (that is, patient does or does not benefit from a particular treatment), rather than granular (e.g., specific dosage or course of treatment) which is much harder to obtain ground truth data.

(b) Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for autonomously predicting an efficacy of a treatment for a patient, the method comprising:

receiving image data of an anatomy of a patient;

obtaining scores for each of a plurality of anatomical features reflected in the image data by applying a feature extraction model that is a first machine learning model to the image data;

applying the scores as input to a treatment model, the treatment model comprising a second machine learning model configured to output a prediction of a measure of efficacy of a particular treatment based on features of the patient's anatomy; and receiving, as output from the treatment model, data representative of the predicted measure of efficacy of the particular treatment.

2. The method of claim 1, further comprising:

determining, based on the image data, a body part to which the image data corresponds; and selecting the feature extraction model from a plurality of candidate feature models based on a concordance between each candidate feature model and a given body part.

3. The method of claim 1, wherein applying the scores as input to the treatment model comprises generating a feature vector that stores, for each anatomical feature of the plurality, its respective identification, and applying the feature vector as input to the treatment model.

4. The method of claim 1, further comprising:

determining, for the particular treatment, whether its predicted measure of efficacy exceeds a threshold; and outputting to a user a recommendation for the particular treatment responsive to determining that its predicted measure of efficacy exceeds the threshold.

5. The method of claim 1, wherein receiving, as output from the treatment model, data representative of the predicted measure of efficacy of the particular treatment comprises receiving, as output from the treatment model, data representative of respective measures of efficacy for each of a plurality of candidate treatments.

6. A non-transitory computer-readable medium comprising instructions encoded thereon for autonomously determining a treatment for a patient, the instructions when executed causing one or more processors to perform operations, the instructions comprising instructions to:

receive image data of an anatomy of a patient;

obtain scores for each of a plurality of anatomical features reflected in the image data by applying a feature extraction model that is a first machine learning model to the image data;

apply the scores as input to a treatment model, the treatment model comprising a second machine learning model configured to output a prediction of a measure of efficacy of a particular treatment based on features of the patient's anatomy; and receive, as output from the treatment model, data representative of the predicted measure of efficacy of the particular treatment.

7. The non-transitory computer-readable medium of claim 6, the instructions further comprising instructions to:

determine, based on the image data, a body part to which the image data corresponds; and select the feature extraction model from a plurality of candidate feature models based on a concordance between each candidate feature model and a given body part.

8. The non-transitory computer-readable medium of claim 6, wherein applying the scores as input to the treatment model comprises generating a feature vector that stores, for each anatomical feature of the plurality, its respective score, and applying the feature vector as input to the treatment model.

9. The non-transitory computer-readable medium of claim 6, the instructions further comprising instructions to:

determine, for the particular treatment, whether its predicted measure of efficacy exceeds a threshold; and output to a user a recommendation for the particular treatment responsive to determining that its predicted measure of efficacy exceeds the threshold.

10. The non-transitory computer-readable medium of claim 6, wherein receiving, as output from the treatment model, data representative of the predicted measure of efficacy of the particular treatment comprises receiving, as output from the treatment model, data representative of respective measures of efficacy for each of a plurality of candidate treatments.

11. A method for autonomously determining a treatment for a patient, the method comprising:

receiving sensor data from an electronic device that monitors a patient;

accessing a machine learning model, the machine learning model configured to output a likelihood that a particular treatment would yield a positive result, where the machine learning model is trained using training data that pairs previously obtained sensor data for a plurality of patients to labels describing whether the particular treatment yielded a positive result for each of the plurality of patients;

applying the received sensor data to the machine learning model; and receiving, as output from the machine learning model, data representative of a likelihood of whether the patient would benefit from the particular treatment.

12. The method of claim 11, wherein the data representative of the likelihood of whether the patient would benefit from the particular treatment comprises a probability that the particular treatment would bring a benefit to the patient, and wherein the method further comprises:

determining, for the particular treatment, whether its corresponding probability exceeds a threshold; and outputting to a user a recommendation for the particular treatment.

13. The method of claim 11, wherein the machine learning model is a convolutional neural network.

14. The method of claim 11, wherein the machine learning model is a multi-task model comprising a shared layer and branches, the shared layer trained to determine one or more candidate diagnoses based on the sensor data, each branch corresponding to a different treatment, each branch trained to output a likelihood that the different treatment to which the branch corresponds will be effective.

15. The method of claim 14, wherein an amount of training data for a branch corresponding to a given treatment is below a threshold, and wherein the multi-task model enriches the amount of training data by back-propagating the training data with information from a different branch.

16. A non-transitory computer-readable medium comprising instructions encoded thereon for autonomously determining a treatment for a patient, the instructions when executed causing one or more processors to perform operations, the instructions comprising instructions to:

receive sensor data from an electronic device that monitors a patient;

access a machine learning model, the machine learning model configured to output a likelihood that a particular treatment would yield a positive result, where the machine learning model is trained using training data that pairs previously obtained sensor data for a plurality of patients to labels describing whether the particular treatment yielded a positive result for each of the plurality of patients;

apply the received sensor data to the machine learning model; and receive, as output from the machine learning model, data representative of a likelihood of whether the patient would benefit from the particular treatment.

17. The non-transitory computer-readable medium of claim 16, wherein the data representative of the one or more treatments comprises probabilities that each of the one or more treatments would bring a benefit to the patient, and wherein the instructions further comprise instructions to:

determine, for each of the one or more treatments, whether its corresponding probability exceeds a threshold; and output to a user a recommendation for each of the one or more treatments that has a corresponding probability that exceeds the threshold.

18. The non-transitory computer-readable medium of claim 16, wherein the machine learning model is a convolutional neural network.

19. The non-transitory computer-readable medium of claim 16, wherein the machine learning model is a multi-task model comprising a shared layer and branches, the shared layer trained to determine one or more candidate diagnoses based on the sensor data, each branch corresponding to a different treatment, each branch trained to output a likelihood that the different treatment to which the branch corresponds will be effective.

20. The non-transitory computer-readable medium of claim 19, wherein an amount of training data for a branch corresponding to a given treatment is below a threshold, and wherein the multi-task model enriches the amount of training data by back-propagating the training data with information from a different branch.

* * * * *